(12) United States Patent
Schetky et al.

(10) Patent No.: US 6,258,182 B1
(45) Date of Patent: Jul. 10, 2001

(54) PSEUDOELASTIC β TITANIUM ALLOY AND USES THEREFOR

(75) Inventors: L. McDonald Schetky, Danbury; Ming H. Wu, Bethel; Chi-Yuan Loi, Easton; Charles J. Burstone, Farmington, all of CT (US)

(73) Assignee: Memry Corporation, Brookfield, CT (US)

( * ) Notice: Subject to any disclaimer, the term of this patent is extended or adjusted under 35 U.S.C. 154(b) by 0 days.

(21) Appl. No.: 09/263,658

(22) Filed: Mar. 5, 1999

Related U.S. Application Data
(60) Provisional application No. 60/076,922, filed on Mar. 5, 1998.

(51) Int. Cl.$^7$ .................................................. C22C 14/00
(52) U.S. Cl. ......................... 148/402; 148/421; 148/671; 420/418; 420/420
(58) Field of Search ................................. 148/407, 421, 148/402, 671; 420/418, 420, 421

(56) References Cited

U.S. PATENT DOCUMENTS

| | | | |
|---|---|---|---|
| 3,986,868 | * 10/1976 | Crossley | 420/421 |
| 4,197,643 | * 4/1980 | Burstone et al. | 148/407 |
| 4,952,236 | * 8/1990 | Wang et al. | 148/421 |
| 5,264,055 | * 11/1993 | Champin et al. | 148/421 |
| 5,358,586 | * 10/1994 | Schutz et al. | 148/421 |
| 5,954,724 | * 9/1999 | Davidson | 148/421 |

OTHER PUBLICATIONS

Hisaoki Sasano et al, Shape Memory Effect in Ti–Mo–Al Alloys, Proceedings of 5th Internatioal Conference on Titanium, Munich, Germany, 1984, pp. 1667–1674.

C.Y. Lei et al, abstract of Development of Pseudoelastic Beta Titanium Orthodontic Wires, International Conference on Displacive Phase Transformations and Their Applications in Materials Engineering, May 1996, 2pp.

C.Y. Lei et al, abstract of A Study of Pseudoelastic Beta Titanium Alloys For Orthodontic Application, Proceedings of the Second International Conference on Shape Memory and Superelastic Technologies, 1997.

* cited by examiner

*Primary Examiner*—George Wyszomierski
(74) *Attorney, Agent, or Firm*—Perkins, Smith, Cohen; Jerry Cohen; Harvey Kaye (57) ABSTRACT

The disclosed β titanium alloys contain alloying elements of molybdenum between 10.0 and 12.0 weight percent, aluminum between 2.8 and 4.0 weight percent, chromium and vanadium between 0.0 and 2.0 weight percent, and niobium between 0.0 and 4.0 weight percent. Orthodontic arch wires and appliances of nickel-free β titanium alloys having pseudo-elastic properties associated with stress-induced martensitic transformation. These arch wires and appliances were found to possess a high strain recovery up to 3.5% strain of deformation, a lower stiffness yielding relatively constant force for tooth movement and improved formability over that of pseudo-elastic nitinol. Eyeglasses having parts made of such materials can be welded. Stents made of this material avoid problems which a certain percentage of the population have when nickel is included within alloys used in the human body. Other medical devices which are used in the body also have this benefit. One of the main benefits of this alloy, is that a certain percentage of the population is sensitive to the presence of Ni and for this reason there has been interest in obtaining a non-NI alloy exhibiting the above super elastic and chemical properties.

25 Claims, 8 Drawing Sheets

PSEUDOELASTIC β TITANIUM ALLOY AND USES THEREFOR

REFERENCE TO RELATED APPLICATIONS

This application claims priority from the U.S. Provisional Application, Ser. No. 60/076,922 filed Mar. 5, 1998.

FIELD OF THE INVENTION

The present invention relates generally to the field of metallurgy and the uses thereof, and, more particularly to shape memory alloys which are particularly suitable for medical uses and which do not use nickel.

BACKGROUND OF INVENTION

Shape Memory Effect and Pseudo-elasticity

Materials which undergo martensite transformation may exhibit "Shape Memory Effect" and "Pseudo-elasticity." During the transformation on cooling, the high temperature phase known as "austenite" changes its crystalline structure through a diffusionless shear process adopting a less symmetrical structure called "martensite", and, on heating, the reverse transformation occurs. The starting temperature of the cooling transformation is referred to as the $M_s$ temperature and the finishing temperature, $M_f$. The starting and finishing temperatures of the reverse transformation on heating are referred to as $A_s$ and $A_f$ respectively.

Materials exhibiting Shape Memory Effect can be deformed in their martensitic phase and upon heating recover their original shapes. These materials can also be deformed in their austenitic phase above the $A_f$ temperature through stress-induced martensitic transformation and recover their original shapes upon unloading. This strain recovery, referred to as "pseudo-elasticity" [sometimes referred to herein as "PE"] is associated with the reversion of stress-induced martensite back to austenite. A well known shape memory alloy is nitinol, a near-stoichiometric alloy of nickel and titanium.

The Alloy Material

Pure titanium has an isomorphous transformation at 882° C. The body centered cubic (bcc) structure, so called β-Ti, is stable above the isomorphous point and the hexagonal close packed (hcp) structure, so called α-Ti, is stable below. When alloyed with elements such as vanadium, molybdenum, or niobium, the resulting alloys have an extended β phase stability below 882° C. On the contrary, when alloyed with elements such as Al or oxygen, the temperature range of stable α phase extends above the isomorphous point. Elements which have the effect of extending the β phase temperature range are called the β stabilizers while those capable of extending the α phase temperature range are called the a stabilizers.

Figure 14:
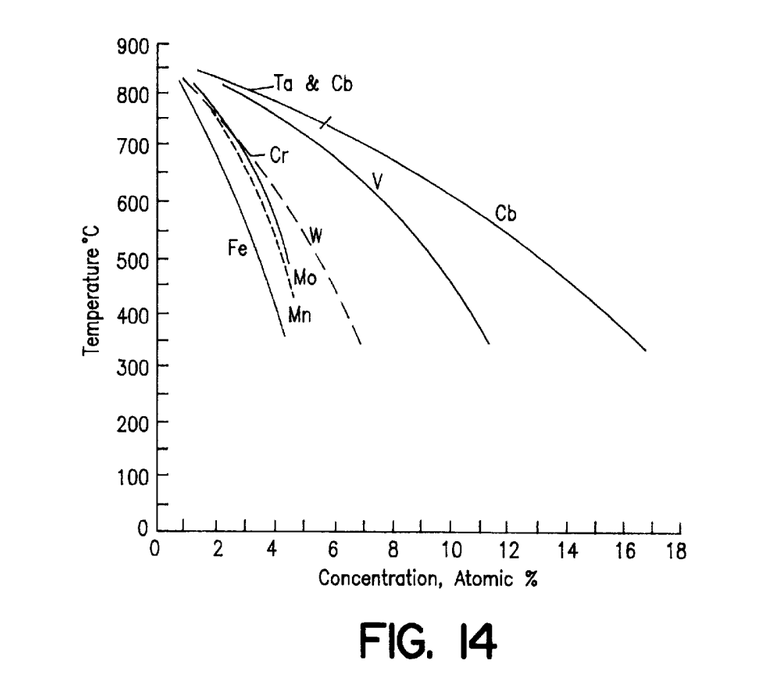
FIG. 14 is a graph showing the dependence of $M_s$ on the concentration of some transition metals in binary titanium alloys.
Figure 15A:
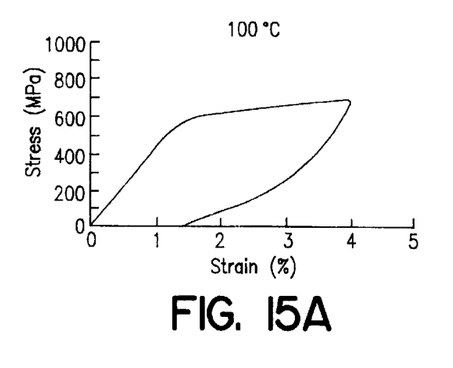
FIG. 15 is a graph showing the stress-strain curves of tensile loading to 4% strain followed by unloading to zero stress of alloy X42025 tested at different temperatures.
Figure 15B:
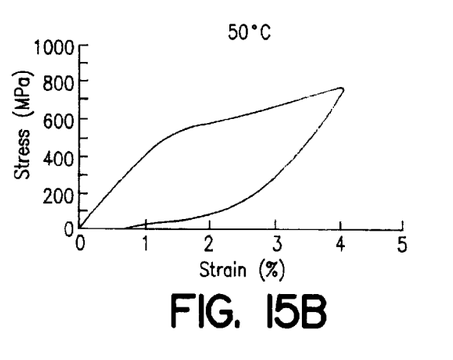
Figure 15C:
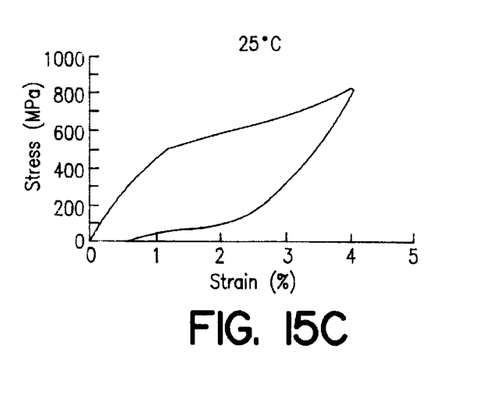
Figure 15D:
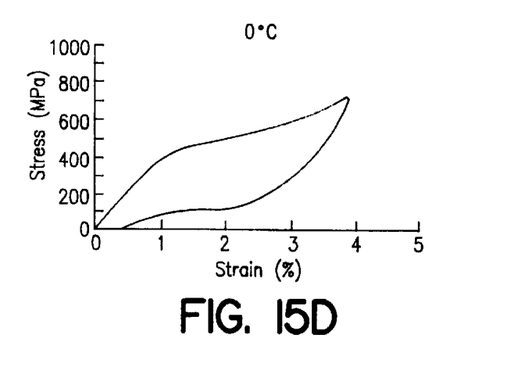
Figure 15E:
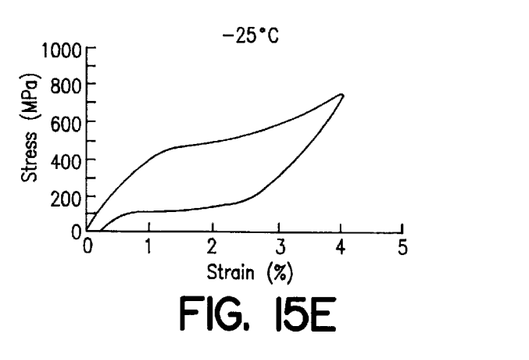

For alloys with a high enough concentration of β stabilizer elements, the material would be sufficiently stabilized to obtain a meta-stable β phase structure at room temperature. The alloys showing such a property are called β titanium alloys. Martensite transformations are commonly found among β titanium alloys. The $M_S$ temperatures in β-Ti alloys decrease with increasing amount of β stabilizer in the alloys, while increasing amount of α stabilizer raises the $M_S$. The dependence of $M_S$ on the concentration of some transition metals in binary titanium alloys is shown in FIG. 14 ['The Martensite Transformation Temperature in Titanium Binary Alloys', Paul Duwez, Trans. ASM, vol. 45, pp.934–940, 1953]. Therefore, depending on the extent of stabilization, β-Ti alloys may exhibit martensitic transformation when cooled very quickly from temperatures above the β transus, the temperatures above which β is the single phase at equilibrium.

To exhibit PE at room temperature, the alloys must be sufficiently β stabilized to have the $A_f$ point suppressed to below the ambient, but still allow the formation of stress-induced martensite before plastic deformation occurs. That is, the stress level for the martensite to form must be lower than that of plastic deformation. Shape memory effect, on the other hand, is observed when an alloy has an $A_s$ point higher than and $M_S$ temperature slightly below room temperature. Stress-induced martensite transformations have also been observed in β titanium alloys ['Formation and Reversion of Stress Induced Martensite in Ti-10V-2Fe-3Al', T. W. Duerig, J Albrecht, D. Richter and P. Fischer, Acta Metall., vol. 30, pp.2161–2172, 1982].

Both shape memory effect and pseudo-elasticity have been observed in certain Ti—Mo—Al β titanium alloys ['Shape Memory Effect in Ti—Mo—Al Alloys', Hisaoki Sasano and Toshiyuki Suzuki, Proc. 5th Int. Conf. on Titanium, Munich, Germany, pp.1667–1674, 1984]. In order to obtain SME or PE at room temperature the material has to be properly heat treated to produce the uniform β phase structure. The heat treatment to achieve that goal is called a solution treatment in which the test sample is heated to temperatures slightly above the β transus for a period of time long enough to allow for full austenization and then immediately cooled to room temperature.

Some β-Ti alloys, for example, TMA (Registered trade mark of Ormco, Glendora, Calif.), has been successfully commercialized for orthodontic arch wire application. The detailed description of the applications and properties of β titanium wires can be found in U.S. Pat. No. 4,197,643. The TMA wires show a unique balance of low stiffness, high spring-back, good formability ['Beta titanium: A new orthodontic alloy', C. Burstone and A. Jon Goldberg, American Journal of orthodontics, pp.121–132, Feb. 1980], and weldability. ['Optimal welding of beta titanium orthodontic wires', Kenneth R. Nelson et al, American Journal of Orthodontics and Dentofacial Orthopedics, pp.213–219, Sept., 1987] The nickel-free chemistry of the alloy makes it more tolerable to some patients. However, TMA wires utilize the inherent mechanical properties of the material through thermo-mechanical processing. The material does not exhibit PE due to the occurrence and reversion of stress-induced martensite in the material.

SUMMARY OF THE PRESENT INVENTION

An object of the present invention is to provide a titanium nickel-free SME alloy which is particularly useful for medical applications.

Another object of the present invention is to provide an alloy having pseudo-elastic properties and which is useful for medical applications.

A further object of the present invention is to provide super-elastic springs made from formable, weldable nickel-free shape memory alloy.

Still a further object of the present invention is to provide shape memory orthodontic springs having constant and readily controlled force.

Yet a further object of the present invention is to provide nickel-free shape memory or pseudo-elastic compositions for use in orthodontic, maxillo-facial and other surgical applications.

These and other objects of the present invention are accomplished by providing a nickel-free β titanium alloy characterized by exhibiting pseudo-elasticity at −25° C. to 50° C. or greater due to the formation and reversion of stress-induced martensite. Such an alloy exhibits SME at room temperature when the $A_S$ temperature is higher than room temperature. Furthermore, the alloy exhibits pseudo-elasticity with lower stiffness and force output magnitude than the conventional β titanium alloy TMA, better formability than Nitinol, the ability to be welded to other appliances, and good corrosion resistance.

It is capable of being cold worked to 20% without significantly reducing the pseudo-elastic performance, whereby it can be cold formed into various shapes at ambient temperature while retaining the high spring-back characteristics of the pseudo-elastic phenomenon, and it can be made so that it exhibits pseudo-elasticity at ambient and/or body temperature. The alloy can have a strain recovery of up to approximately 3.5% when tensile loaded to 4% strain at room temperature in the as-solution treated condition. The nickel-free β titanium alloy can be used for a medical device within a living body, such as an orthodontic arch wire, a stent, a catheter introducer, oral pins and/or plates used in maxillofacial reconstructive procedures, oviduct clamp, and bone staples, for example. It can also be used for eyeglasses. A nickel-free β titanium having superelastic properties by being cold worked in its martensitic state, said alloy exhibiting complete elastic behavior at strains up to 4%, thereby permitting the designing of medical instruments and devices which are resistant to permanent deformation or kinking. It can be used for a medical device comprising a small coil capable of being stretched to assume an almost linear shape which allows it to be placed inside a medical catheter for delivery to a desired site in the human body and when discharged from the catheter the wire will assume its original coil form to perform the function of a stent. The composition can be used for a catheter guide wire characterized by great resistance to kinking and possessing excellent torquing (each end twists the same amount, thereby transferring torque accurately).

The nickel-free β titanium alloy may be formed from:
(a) between 10.0 and 12.0 wt. % molybdenum;
(b) between 2.8 and 4.0 wt. % aluminum;
(c) chromium and vanadium between 0.0 and 2.0 wt. % chromium and vanadium; and
(d) between 0.0 and 4.0 wt.% niobium; and
(e) the balance titanium.

There may be a balanced amount of the alloying elements, and an effective amount of at least one selected from the group consisting of chromium, vanadium and niobium.

In one arrangement it may be formed of molybdenum of 10.2 wt. %, aluminum of 2.8 wt. %, vanadium of 1.8 wt. %, niobium of 3.7 wt.% and the balance of titanium and exhibit pseudo-elasticity between 25 and −25° C.

In another arrangement it may be formed of molybdenum of 11.1 wt. %, aluminum of 2.95 wt. %, vanadium of 1.9 wt. %, niobium of 4.0 wt. % and the balance of titanium and exhibit pseudo-elasticity between 50 and −25° C.

It is also a method for making a nickel-free β titanium alloy, comprising the steps of alloying together:
(a) between 10.0 and 12.0 wt. % molybdenum;
(b) between 2.8 and 4.0 wt. % aluminum;
(c) chromium and vanadium between 0.0 and 2.0 wt. % chromium and vanadium; and
(d) between 0.0 and 4.0 wt. % niobium; and
(e) the balance titanium.

In this method the alloy can be cold worked up to 20% without significantly reducing the pseudo-elastic performance, whereby the alloy is capable of being cold formed into various shapes at ambient temperature while retaining the high spring-back characteristics of the pseudo-elastic phenomenon. Orthodontic Appliances The purpose of orthodontic appliances is to correct teeth irregularities and/or abnormalities in their relationships with surrounding members. This is achieved by using elastically deformed wires which impart forces to the targeted teeth and cause movements during the wire's unloading process.

Orthodontic materials have evolved over the years from simple stainless steels to high modulus cobalt alloys, low modulus titanium alloys of linear elasticity and duplex wires using either twisted, braided or coaxial configurations. Materials suitable for orthodontic appliance applications preferably possess a combination of high spring-back, low stiffness, reasonable formability, good corrosion resistance, and the ability to be readily joined to other components.

PE phenomenon has not been utilized in orthodontic arch wire application with the exception of NiTi alloy. NiTi, with its exceptionally high strain recovery of up to 8%, has long been used as orthodontic wire material, as was described in U.S. Pat. No. 4,037,324. But the material suffers from poor formability, difficulty in joining with other appliances, and a concern over nickel's toxicity. The availability of a low stiffness pseudo-elastic nickel-free wire with better forming characteristics and the ability to be joined to other appliances would be of great value to the practicing orthodontist.

It has been recognized that optimal tooth motion is accomplished by the application of a low and constant force on the teeth, thus avoiding root resorption and hyalinization of the periodontal ligament which inhibit tooth motion. The control of the force delivered by the orthodontic appliance can be of two forms, variable cross section wire or variable modulus wires. The latter approach, referred to as variable-modulus technique [C. J. Burstone, American J. Orthodontics, vol. 80, 1981, p1.], has proven more popular with the availability of wires having a wide variety of elasticity and stiffness. Instead of using one type of wire material and varying the desired mechanics by changing the wire dimension, variable-modulus technique has the freedom in selecting wire material which yields the optimum force/deflection characteristics for each stage of the orthodontic practice while maintaining the same wire dimension. This technique significantly reduces appliance complexity and creates greater flexibility in clinical practices.

Stents

Stents are fabricated from coiled wire springs or from laser cut tube and are used to repair the patency of previously weakened, narrowed, ballooned or other wise defective or impaired lumen or other body channels. They are deployed by the use of a catheter in laproscopic procedures. Examples are: blood vessels, bile duct, esophagus, urethra, trachea and the like. Specifically: interluminal lining of Aortic Abdominal aneurysms, iliac or femoral aneurysms, recanalization of injured vessels caused by blunt or penetrating trauma, dilation and recanalization of stenotic arterial segments, tampanade and obliteration of esophageal varices, recanalization of esophageal stenoses secondary to carcinoma or benign strictures, ureteral strictures and tracheal strictures. In all these applications a nickel free superelastic or shape memory alloy offers freedom from possible patient reaction to nickel.

Catheter Introducers

Interventional cardiovascular procedures require the use of catheters to bring to the area of interest either instruments for measuring and observing the affected area or to deploy stents. The tortuous paths of many of the body vessels require the use of a guiding system to make possible the continuous advance of the catheter; these guide wires are called catheter introducers and two characteristics are required: flexibility and freedom from any tendency to kink and the ability to faithfully transmit a twisting motion from the distal to the proximal end. Super-elastic shape memory alloy wires have demonstrated these characteristics and are the preferred material for construction. It is often desirable to weld to the guide wire some type of ending or handle; the nickel free alloys of the present invention offer weldability far superior to conventional nickel titanium shape memory alloys. In addition, if necessary they can the formed at the operating site to accommodate special requirements of the surgeon.

Oral, Maxillofacial Reconstructive Procedures Using Pins And Plates

Many cosmetic procedures such as reshaping mandible, frontal bones, nose, and cranial features frequently require auxiliary fixtures to support the new position during bone setting. Since in some cases these plates and fixtures may be left in place, nickel free shape memory or super-elastic alloys would be advantages.

Oviduct Clamp

The clamping of a fallopian tube using endoscopic procedures is well established and the use of shape memory clamps is a preferred technique. To avoid the possibility of nickel sensitive reaction, given the long dwell time for such a device, a nickel-free shape memory alloy clamp would provide a drastic reduction in the risk of the procedure.

Bone Staples

Shape memory staples have been proposed for bringing into close proximity fractured surfaces of various bones. Healing time is considerably improved by this technique, but questions of tissue reaction remain when using nickel-containing shape memory alloys. A nickel-free shape memory or super-elastic alloy would allay concerns over such a reaction in staples which will have a long dwell time in the body.

The advantages referred to the above noted uses are examples and many other similar surgical devices can benefit from a nickel-free shape memory or PE alloy. Examples of environments in which the alloy of the present invention could be used are disclosed in the following U.S. Pat. Nos. 4,503,569 for a graft prosthesis, 155,147,370 for a stent, 5,466,242 for a stent for biliary, urinary or vascular system, 5,653,689 for an infusion catheter, 5,830,179 for a urological stent.

Other objects, features and advantages will be apparent from the following detailed description of preferred embodiments taken in conjunction with the accompanying drawings in which:

DETAILED DESCRIPTION OF THE INVENTION

All of the sample alloys in the matrix discussed below were prepared by double vacuum arc melting technique, the ingots were hot rolled and flattened to sheets of 1.27 mm in thickness. Oxides on the sheets were removed by double-disc grinding and lapping. The test specimens were cut from sheets and sealed in evacuated quartz tubes back-filled with argon. The capsules were then heater to 880° C. for 30 minutes and quenched into a water bath at ambient temperature. Aging experiments were conducted at 200, 300 and 400° C. using a nitride/nitrade salt bath.

Permanent deformation and pseudo-elastic recovery strains were determined by bend tests. Specimens, 0.51× 1.02×51 mm in dimension, were cut from the sheets and then solution treated. After heat treatment, the specimens were bent against rods of different radii to form a "U" shape. The angles between the straight portions were measured afterwards and the strain recovery calculated to be:

$$e(rec)=e(180-a)/180;$$

where "a" is the unrecovered angle and "e" is the outer-fiber bending strain.

Tensile strain recovery was measured by tensile elongation to 4% strain followed by unloading to zero stress. Dogbone tensile specimens with a cross sectional dimension of 0.90 mm×2.0 mm were used and the strain was monitored using an extensometer. An environmental chamber with electrical heating and $CO_2$ cooling capabilities provides a range of test temperature from −30° C. to 180° C.

The bending moment/deflection characteristics of orthodontic wire were determined by flexural tests at a university laboratory. Specimens 0.41×0.56 mm in cross section were used. A torque gauge apparatus was used to apply an angular deflection to the wires. The angular deflection of the specimens was measured with a protractor. The couple necessary to create the angular displacement was resisted by a force at the free end through an anvil placed against the specimens. A 5 mm span length was used for all the tests.

Figure 1:
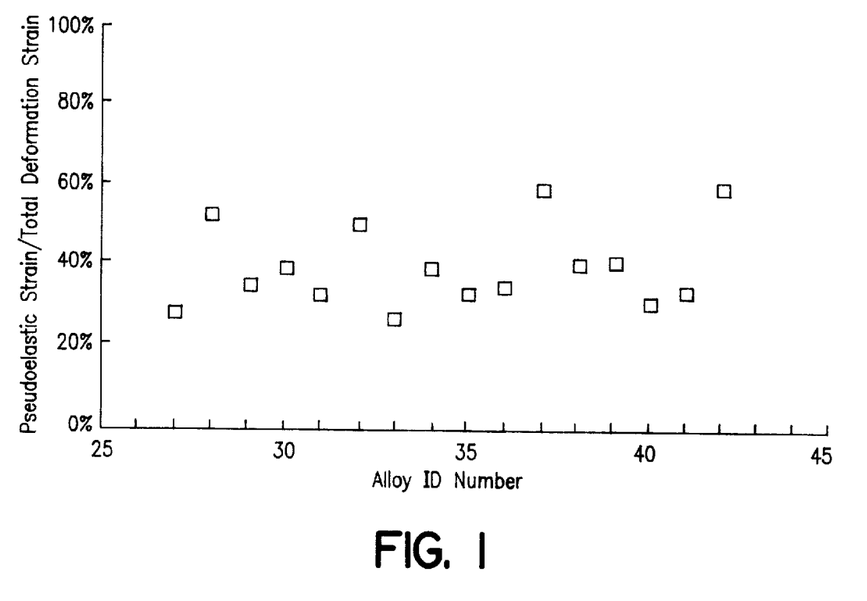
FIG. 1 is a graph showing the percentages of pseudo-elastic recovery strain relative to the bending strain for the fifteen alloys.

Bend tests at 6% bending strain were used for screening the alloys for their pseudo-elastic properties. The percentages of pseudo-elastic recovery strain relative to the bending strain for the fifteen alloys (one alloy was out-of-range and therefore was not used) are plotted in FIG. 1. Among the alloys, #42 exhibited the highest pseudo-elastic strain recovery and was selected for further studies.

Figure 2:
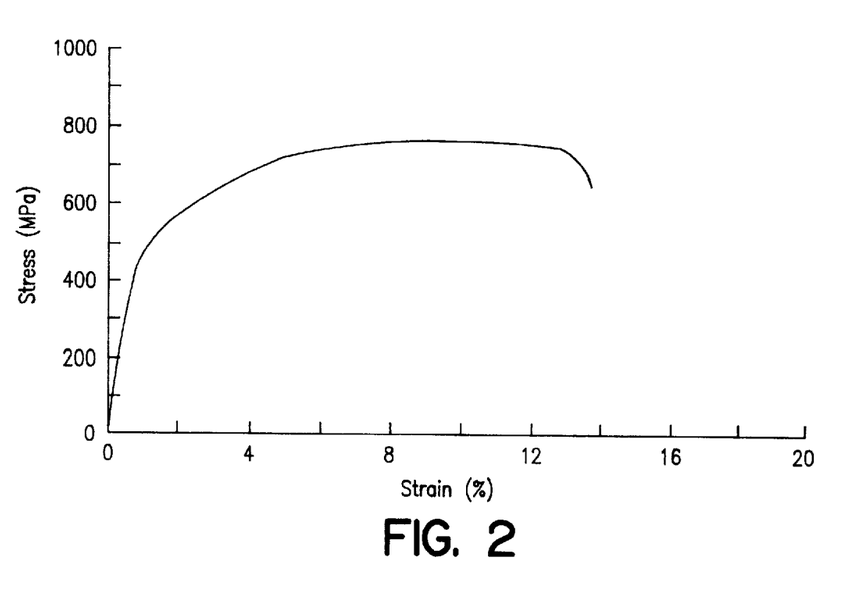
FIG. 2 is a graph showing a tensile stress-strain curve for alloy #42 tested to failure.
Figure 3A:
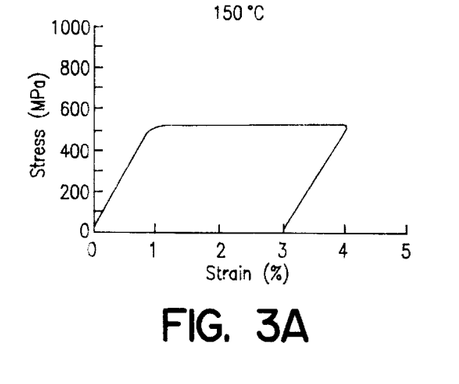
FIG. 3 is a graph showing stress-strain curves of tensile loading to 4% strain followed by unloading to zero stress of alloy #42 tested at different temperatures.
Figure 3B:
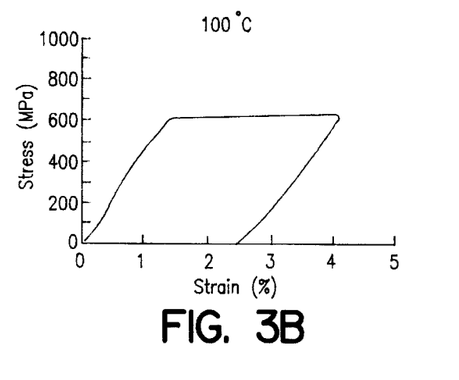
Figure 3C:
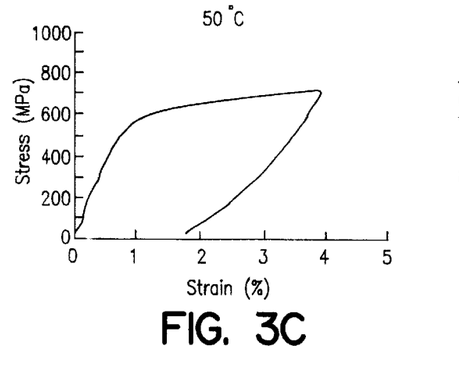
Figure 3D:
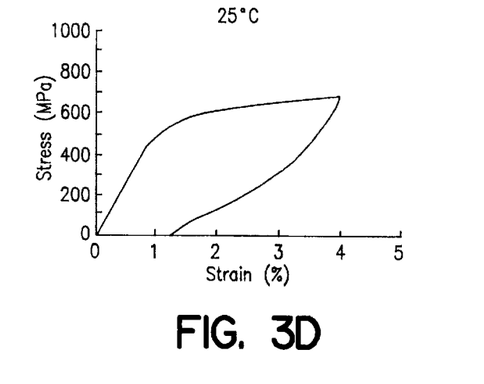
Figure 3E:
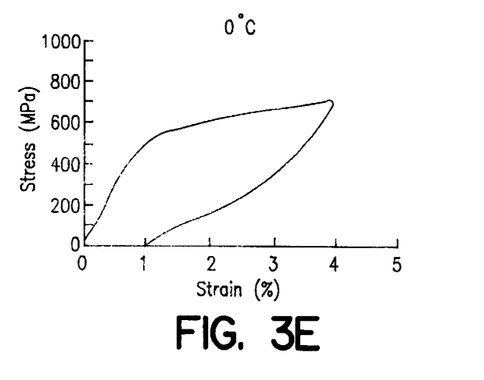
Figure 3F:
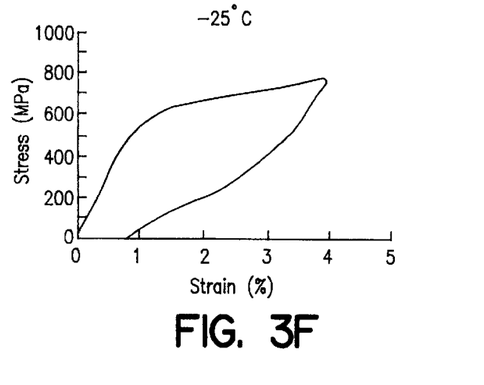

FIG. 2 shows a tensile stress-strain curve of alloy #42 tested to failure. The mechanical properties based on the curve are summarized in Table I. In absence of significant work hardening, the reduction in cross-section area (R.A.) is much higher than the tensile elongation and is a better indication of the true ductility of the alloy.

TABLE I

Mechanical properties of alloy #42.

| UTS | Yield Stress | Young's Modulus | R.A. | Tensile Elongation |
|---|---|---|---|---|
| 765 MPa | 500 MPa | 65 GPa | 27% | 13.7% |

Tensile loading/unloading hysteresis curves for alloy #42 tested to 4% strain at temperatures from −25° C. to 150° C. are shown in FIG. 3.

A matrix of fifteen β titanium alloys with the composition range (wt. %) listed in Table II. were examined.

TABLE II

|  | Mo | Al | Cr | V | Nb |
|---|---|---|---|---|---|
| Low | 9.5 | 2 | 0 | 0 | 0 |
| High | 12 | 4 | 2 | 2 | 4 |

The alloys use molybdenum as the major β stabilizer and aluminum as the major α stabilizer. Their chemical compositions are listed in Table III. All specimens were subjected to a standard solution treatment of 10 minutes at 800° C. followed by quenching into a water bath at room temperature. Bend test results of as-solution treated specimens in Table III. show the alloys which exhibit SME or PE at room temperature. Out of the fifteen alloys screened, alloys #28, 32, 37, and 42 exhibited significant pseudo-elastic strain recovery, while alloys #31, 33 and 41 exhibited SME.

TABLE III

| Alloy ID | Mo | Al | Cr | V | Nb | ES (%) | SME (%) | PD (%) |
|---|---|---|---|---|---|---|---|---|
| 27 | 9.5 | 3.1 | 1.4 | 1.4 | 3.1 | 1.6 | 0 | 4.3 |
| 28 | 10.0 | 3.5 | 1.7 | 0 | 0 | 3 | 0 | 2.9 |
| 29 | 9.0 | 2.3 | 1.4 | 0 | 3.0 | 2 | 0.1 | 4 |
| 30 | 10.3 | 2.7 | 1.8 | 1.6 | 0 | 2.3 | 0.1 | 3.7 |
| 31 | 11.8 | 3.7 | 0 | 0 | 0 | 1.9 | 3.5 | 0.7 |
| 32 | 11.0 | 2.8 | 0 | 1.8 | 3.6 | 3.1 | 0.1 | 3.1 |
| 33 | 10.4 | 3.6 | 0 | 1.8 | 3.7 | 1.7 | 3.8 | 0.9 |
| 34 | 10.2 | 2.7 | 0 | 0 | 0 | 2.1 | 0 | 3.4 |
| 35 | 11.5 | 3.7 | 1.8 | 0 | 0 | 1.8 | 0 | 3.8 |
| 36 | 8.4 | 3.0 | 1.4 | 1.4 | 3.0 | 2 | 0.1 | 4 |
| 37 | 11.6 | 2.8 | 1.8 | 1.8 | 0 | 3.4 | 0 | 2.5 |
| 38 | 10.4 | 2.6 | 1.8 | 1.8 | 3.7 | 2.3 | 0.1 | 3.5 |
| 39 | 11.6 | 3.6 | 0 | 1.8 | 3.8 | 2.6 | 0.1 | 3.7 |
| 41 | 11.5 | 2.8 | 0 | 0 | 0 | 1.8 | 3.5 | 0.5 |
| 42 | 10.2 | 2.8 | 0 | 1.8 | 3.7 | 3.7 | 0.5 | 2.2 |

Figure 4:
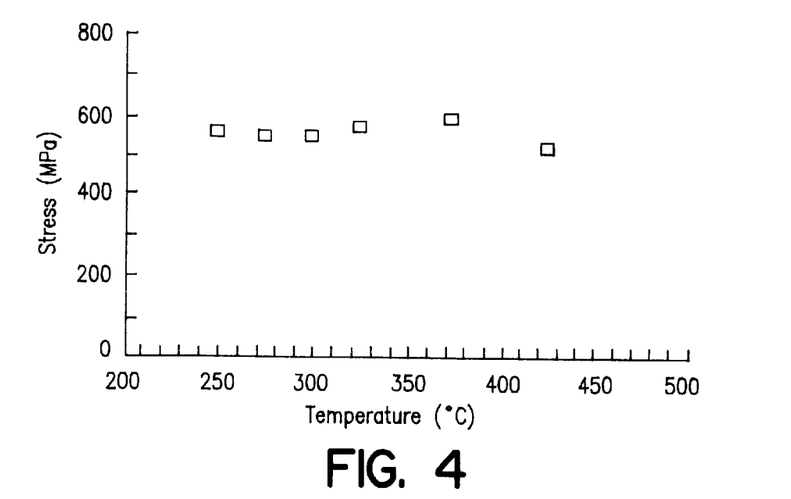
FIG. 4 is a plot showing the effect of temperature on the first yield of alloy #42.

ES - elastic spring-back
SME - shape memory strain recovery on heating
PD - permanent plastic deformation The tensile loading-unloading test gives accurate quantitative results on strain recovery and modulus, and therefore is a widely accepted way of characterizing materials exhibiting SME and PE. Stress-strain curves of tensile loading to 4% strain ed by unloading to zero stress tests on alloy #42 are shown in FIG. 3. Distinctive PE was observed in the temperature range between −25 and 25° C. Effects work on the PE of alloy #42 were also studied by bend tests. The bend test indicate that cold work up to 20% of as-solution treated specimens does not the strain recovery significantly (FIG. 3) where the temperatures range from −25° C. to 150°C. well defined pseudo-elasticity was observed at temperatures below 25 ° C. The residual plastic deformation decreases as pseudo-elasticity becomes more pronounced with decreasing temperatures. The yield stress (critical stress to induce martensite) is relatively insensitive to the temperature as it decreases only slightly with decreasing temperature (FIG. 4).

Figure 5:
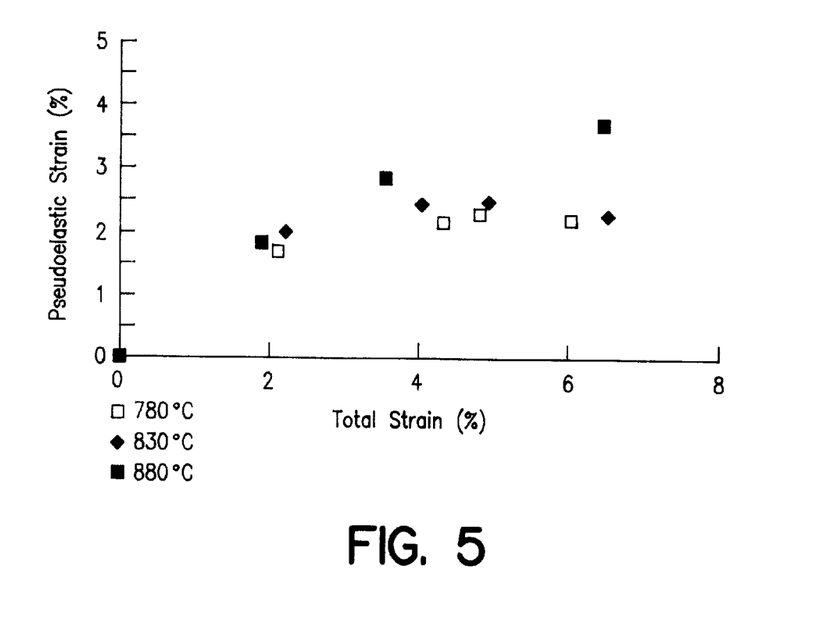
FIG. 5 is a plot of bend test results of alloy #42 showing the effect of solution treatment temperature on the strain recovery by bending.

The bend test results of #42 after solution-treatment at 880° C., 830° C. and 780° C. for 30 minutes are shown in FIG. 5. Specimens heat treated at temperatures lower than 880°C. resulted in lower amount of pseudo-elastic strain recovery.

Figure 6:
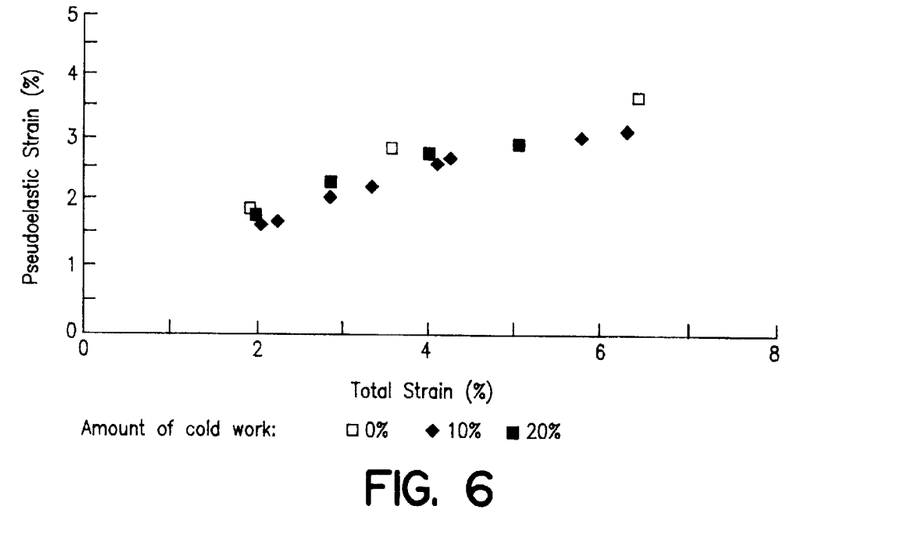
FIG. 6 is a plot of the pseudo-elastic recovery strain during bend tests of the cold-rolled samples.

Solution-treated sheets of alloy #42 were cold rolled to thicknesses with 10% and 20% reduction. The pseudo-elastic recovery strain during bend tests of the cold-rolled samples are plotted in FIG. 6. It can be seen that pseudo-elastic strain recovery decreases only slightly as a result of increasing amount of cold work, indicating that pseudo-elasticity in this alloy is not significantly affected by cold deformation up to 20%.

Figure 7:
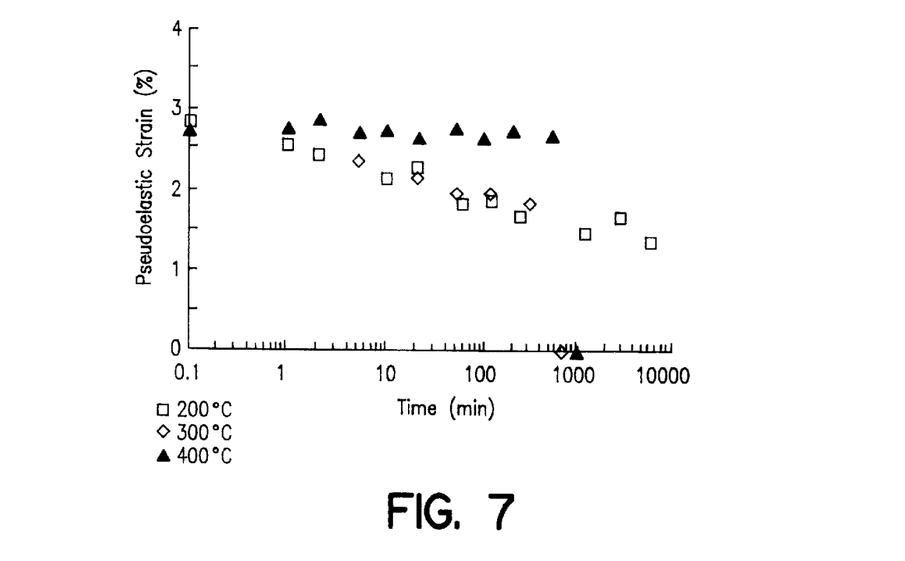
FIG. 7 is a plot of pseudo-elastic recovery strains of specimens after aging at 200, 300 and 400° C. against aging time.

Effects of aging at temperatures from 200 to 400° C. were studied by bend tests to 4% total outer-fiber bending strains. Pseudo-elastic recovery strains of specimens after aging at 200, 300 and 400° C. are plotted against aging time in FIG. 7. The pseudo-elastic recovery strain decreases from the as-solution-treated level of 2.8% to approximately 1.5% after one day of aging at 200° C. and to about 1.8% after five hours of aging at 300° C. It was also noted that ductility of the alloy decreases significantly during aging at these temperatures. The reductions in area measured after tensile test specimens with selected aging condition are listed in Table IV. Bend test specimens after aging at 300° C. for 600 minutes and 400° C. for 1000 minutes broke at 4% bending strain during the tests.

TABLE IV

Area (R.A.) of alloy #42 after aging treatment.

| Aging Treatment | R.A. |
|---|---|
| 200° C./50 hrs. | 12.6% |
| 300° C./60 min. | 14.1% |
| 300° C./100 min. | 9.5% |

The aging embrittlement at these low temperature is most likely related to the formation of ω-phase as two of the effects of ω-phase observed by Duerig et al, i.e., low work hardening and low ductility, are also observed in the specimens aged at 200 and 300° C.

Figure 9:
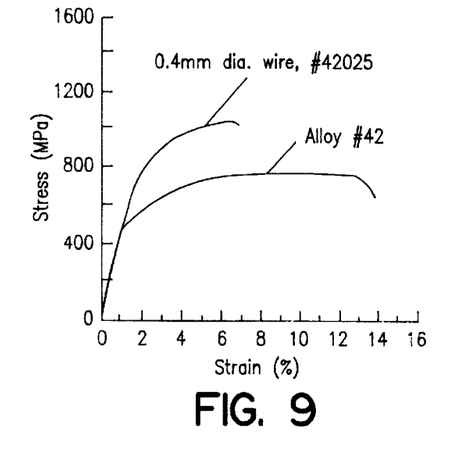
FIG. 9 tensile stress-strain curves of alloy #42025 and dogbone specimen of alloy #42.

The tensile stress-strain curves of alloy #42 as well as 0.4 mm diameter wire of alloy #42025 tested to failure are shown in FIG. 9. The tensile elongation of the #42025 specimen in the as-solution-treated condition is approximately 7 percent which is approximately half of what was obtained from #42 specimen. The ultimate tensile strength of the wire specimen is about 1000 MPa, significantly higher than that of #42, which is around 780 MPa. The mechanical properties based on the test data are summarized in Table I. In the absence of significant work hardening, the reduction in cross-section area (R.A.) is much high than the tensile elongation and is a better indication of the true ductility of the alloy.

Figure 10:
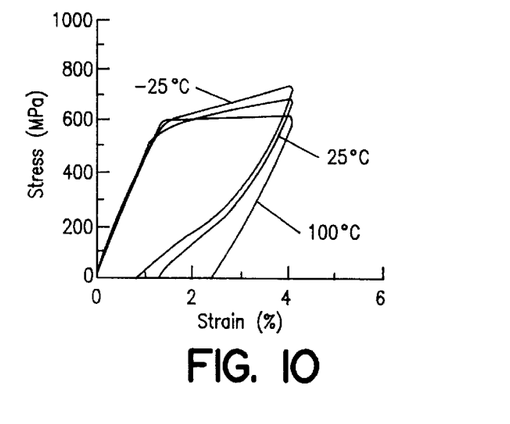
FIG. 10 tensile hysteresis curves of alloy #42 at three different temperatures.
Figure 11:
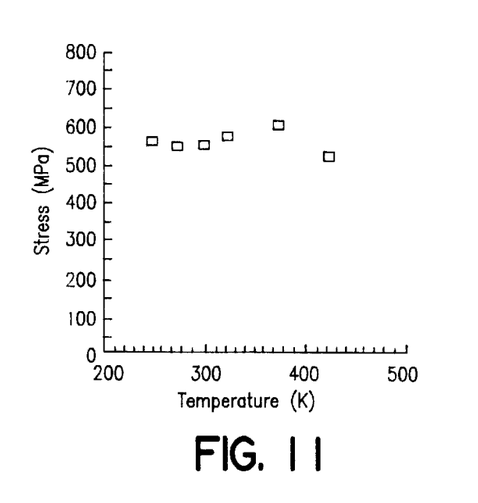
FIG. 11 yield stress of alloy #42 at different temperatures.

Tensile hysteresis curves tested to 4% strain at temperatures at −25, 25 and 100° C. are shown in FIG. 10. Well defined pseudo-elasticity was observed at temperatures below 25° C. The yield stress (critical stress to induce martensite) is relatively insensitive to the temperature as it decreases only slightly with decreasing temperature (FIG. 11). This indicates that the $A_f$ point of this alloy is below room temperature and $M_d$, the temperature above which PE cannot take place, is close to 100° C.

Figure 12:
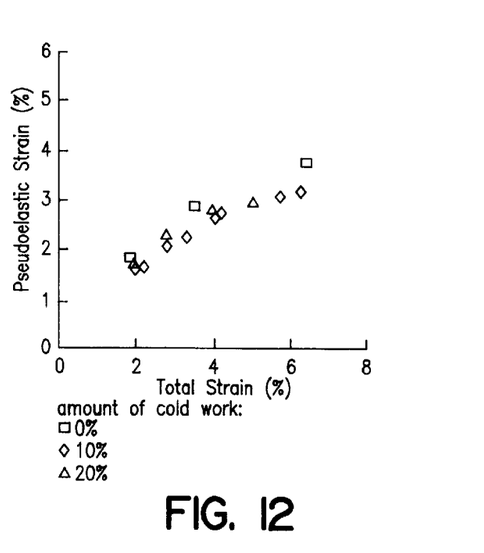
FIG. 12 effect of cold work on the pseudo-elastic strain of alloy #42.

Solution-treated sheets of alloy #42 were cold rolled to thickness with 10% and 20% reduction. The pseudo-elastic recovery strain by bend tests of samples with and without cold work are plotted in FIG. 12. It can be seen that pseudo-elastic strain recovery decreases only slightly as a result of increasing amount of cold work, indicating that pseudo-elasticity in this alloy is not significantly affected by cold deformation up to 20%.

The new alloy, X42025, based on the composition of alloy #42 was melted and processed to wires of 0.061" and 0.016" diameter. The wet chemical analysis showed that the alloy has a chemical composition of: Ti- 11.14 wt. % Mo- 2.95 wt. % Al- 1.88 wt. % V- 3.99 wt. % Nb. The tensile loading to 4% strain followed by unloading to zero stress curves of alloy X42025 are shown in FIG. 15. Again, the alloy exhibits distinct PE between −25° C and 50° C.

Comparing the chemical compositions of alloys #42 and X42025, it is noted that even though the composition of molybdenum in X42025 is almost one percent higher than that of alloy #42, both exhibit significant PE in a quite similar temperature range. Since the martensite transformation temperatures are very sensitive to the molybdenum content, it is clear that a wide $A_f$ range exists for the alloys to exhibit PE at room temperature. By examining the chemical compositions of alloys with PE or SME, it is recognized that alloys with chemical compositions within the boundaries of: molybdenum between 10.0 and 12.0 wt. %, aluminum between 2.8 and 4.0 wt. %, chromium and vanadium between 0.0 and 2.0 wt. %, and niobium between 0.0 and 4.0 wt. %, would exhibit PE or SME when the transformation temperatures, decided by the proper balance of α and β stabilizers, fall in the right temperature range. With the experimental data available one skilled in the art can define the transformation temperature or operating temperature range required for either SME or PE.

Solution-treated sheets of alloy #42 were cold rolled to thickness with 10% and 20% reduction. The pseudo-elastic recovery strain by bend tests of samples with and without cold work are plotted in FIG. 12. It can be seen that pseudo-elastic strain recovery decreases only slightly as a result of increasing amount of cold work, indication that pseudo-elasticity in this alloy is not significantly affected by cold deformation up to 20%.

A good way to compare the mechanical performance between pseudo-elastic β titanium and other commercial orthodontics arch wire materials is by the flexural test. Flexural tests produce the bending moment—activation angle curves which allow us to compare the relative force output, stiffness and spring-back among different wire materials; and therefore is important for the quantitative evaluation of a new alloy for orthodontic applications. Flexural tests provide a direct comparison of bending moment-activation angle relationship among a variety of arch wire materials, which is an important quantitative evaluation of a new alloy for the application of orthodontic arch wire. The flexural test curves of 8 stainless steel, Nitinol, TMA and alloy #42 of FIG. 8 indicates that alloy #42 has a combination of desirable characteristics. Alloy #42 has a spring-back characteristic comparable to that of TMA, which is between those of stainless steel and Nitinol. The force output, on the other hand, is similar to that of Nitinol. The data suggested that alloy #42 has the desirable combination of the following properties, a similar spring-back characteristics together with a lower stiffness when compared to those of TMA and better formability than that of Nitinol.

Figure 8:
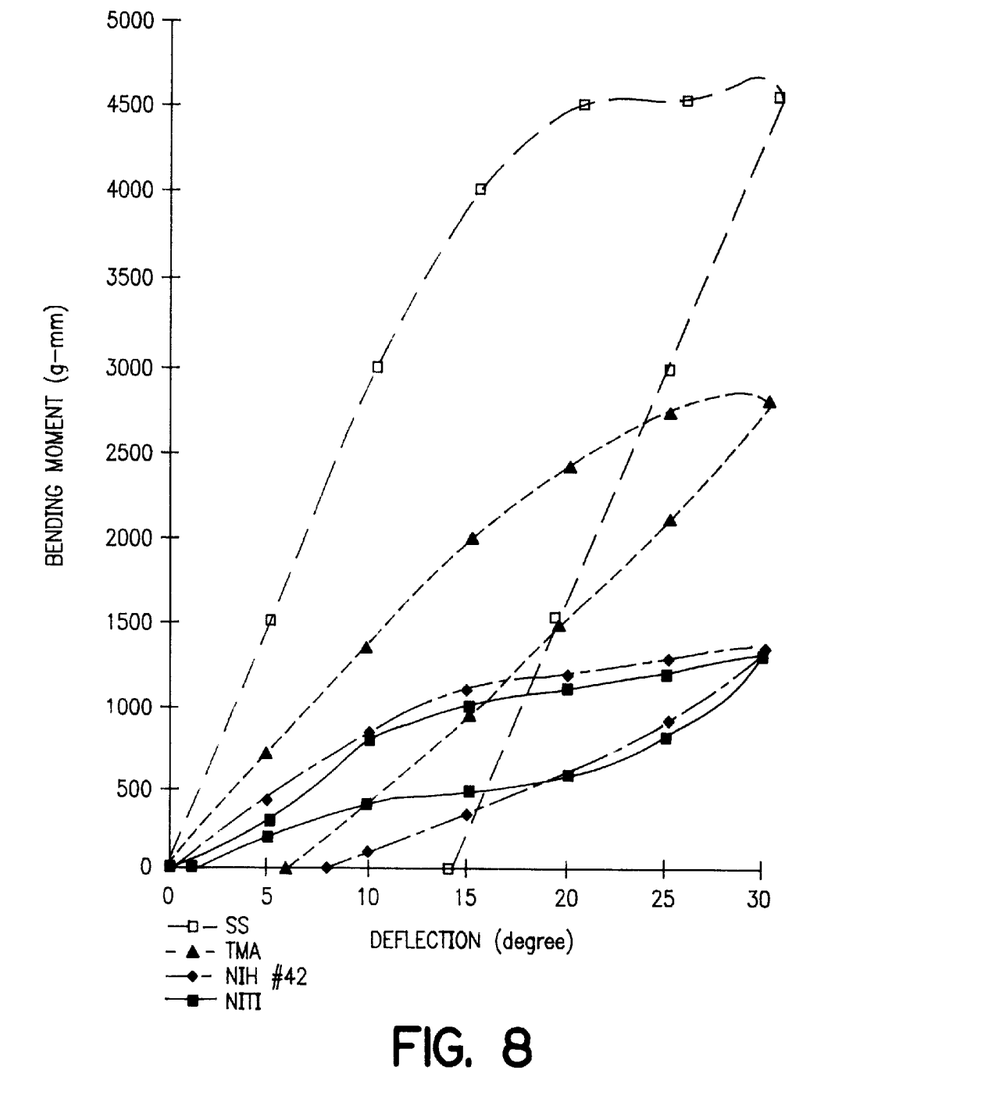
FIG. 8 is a comparison of the flexural test data of stainless steel, TMA, nitinol and present alloy #42.

A detailed description of the test setup and method can be found in previous literature. ['Chinese NiTi wire-A new orthodontic alloy', by Charles J. Burstone et al, American Journal of Orthodontics, pp. 445–452, Jun., 1985] Flexural test curves of 8 stainless steel, Nitinol, TMA and alloy #42 are depicted in FIG. 8. The flexural test data indicates that alloy #42 has a combination of the following properties; a similar spring-back characteristics together with a lower stiffness when compared to those of TMA and better formability than that of Nitinol.

Figure 13:
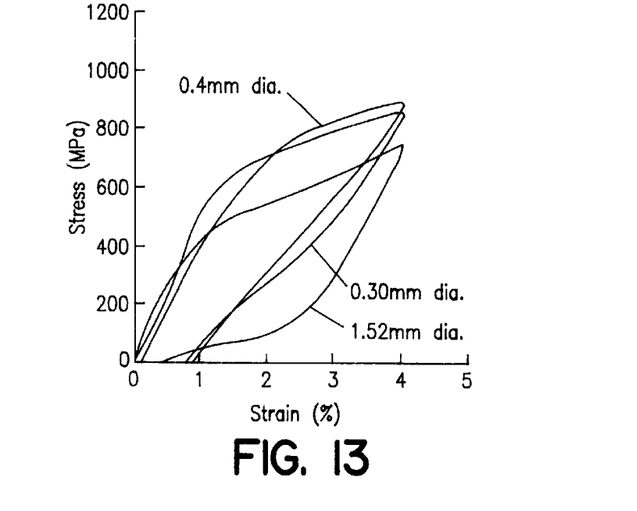
FIG. 13 is a graph of the 15 tensile hysteresis curves of as-solution treated wires of alloy #42025.

Part of the #42025 forged bar was cold drawn with inter-pass vacuum annealing down to wires of 1.52 mm and 0.40 mm in diameter with approximately 30% retained cold reduction in cross-section area. The pilot size trial for the production of alloy #42025 demonstrated that the alloy can be successfully processed to the desired size for orthodontic applications. The room temperature tensile hysteresis curves of 0.40 mm and 1.52 mm diameter wires in the as-quenched condition are shown in FIG. 13. Distinct pseudo-elasticity can be seen on the curve of 1.52 mm wire but almost nonexistent on the 0.40 mm wire curve.

A layer of contaminated structure was observed on the surface of the 0.40 mm wire but not on 1.52 mm wire sample. The surface layer of a piece of 0.40 wire was mechanically polished to approximately 0.30 mm diameter followed by solution treatment in argon. The resulting tensile hysteresis curve showed some improvement in pseudo-elasticity (FIG. 13).

The surface layer is believed to be α phase caused by oxygen infiltration during hot processing in air and is detrimental to the pseudo-elasticity of the alloy. Therefore, the production process needs to avoid extended high temperature exposure in any oxygen-containing atmosphere, especially in the latter stage of wire drawing to obtain materials with high pseudo-elastic springback for the orthodontic applications.

Comparing the tensile hysteresis curves of #42 and 1.52 mm diameter wire of #42025, it is believed that, with optimized composition as well as a proper production and heat treating process, this material significantly improves its pseudo-elastic properties making it a more versatile and competitive material in orthodontic, and other medical applications.

Alloy #42 as well as alloys of its class has a unique place in orthodontic usage. It is highly formable without adverse effect on pseudo-elasticity which allows the fabrication of complex anchors, loops, and springs and their modification at chairside by the orthodontist to individualize treatment. Steel and titanium wires are also formable; however their force levels are much higher for full wire-attachment engagement. Alloy #42 has applications in initial leveling or alignment where moderate discrepancies exist, low forces are needed, and bends are placed to reduce side effects, overtreat, and to individualize arch forms.

Thus, a pseudo-elastic titanium alloy based on Ti—Mo—Al has been developed. The alloy, when properly solution treated, exhibits a well-defined pseudo-elastic behavior which is insensitive to decreasing temperature below the ambient. The pseudo-elastic behavior of the alloy is not significantly affected by cold work up to 20% reduction. Aging of the present alloy at temperatures in the range of 200 to 400° C. results in decrease of pseudo-elastic strain recovery and loss in ductility. The alloy possesses desirable properties of good spring-back, low stiffness, and good formability for orthodontics arch wire application. When compared with other commercial orthodontics arch wires, the present alloy exhibits spring-back similar to that of TMA and stiffness similar to that of nitinol. Orthodontics arch wires of the present alloy is ideal for the intermediate stage of orthodontic treatment.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. A substantially nickel-free β titanium alloy comprising:
   (a) between 10.0 and 12.0 wt. % molybdenum;
   (b) between 2.8 and 4.0 wt. % aluminum;
   (c) chromium and vanadium each between 0.0 and 2.0 wt. %; and
   (d) between 0.0 and 4.0 wt. % niobium; and
   (e) the balance titanium, there being at least one element selected from the group consisting of chromium, vandadium, and niobium.

2. An alloy as defined in claim 1 characterized by exhibiting pseudo-elasticity in the range of −25°C. to 50° C.

3. An alloy as defined in claim 2, which exhibits shape memory effect when deformed at room temperature and subsequently subjected to heating.

4. An alloy as defined in claim 2 which exhibits pseudo-elasticity between 25 and −25° C.

5. An alloy as defined in claim 4, which has a strain recovery of approximately 2.7% when tensile loaded to 4% strain at room temperature in the as-solution treated condition.

6. An alloy as defined in claim 2 formed into an orthodontic arch wire, springs, implants or endodontic files.

7. An alloy as defined in claim 2 formed into eyeglasses.

8. An alloy as defined in claim 2 formed into a medical device for use within a living body.

9. An alloy as defined in claim 8 wherein said medical device is chosen from the following group: (1) a stent; (2) a catheter introducer; (3) oral pins and/or plates used in maxillofacial reconstructive procedures; (4) oviduct clamp; and (5) bone staples.

10. An alloy as defined in claim 1 capable of being cold worked up to 20% without significantly reducing the pseudo-elastic performance, whereby it is capable of being cold formed into various shapes at ambient temperature while retaining the high spring-back characteristics of the pseudo-elastic phenomenon.

11. An alloy as defined in claim 1 which exhibits pseudo-elasticity at ambient and/or body temperature.

12. An alloy as defined in claim 11, which has a strain recovery up to approximately 3.5% when tensile loaded to 4% strain at room temperature in the as-solution treated condition.

13. An alloy as defined in claim 11 characterized by exhibiting almost complete elastic behavior when deformed up to 4%, thereby permitting the designing of medical instruments and devices which are resistant to permanent deformation.

14. An alloy as defined in claim 1, comprising, molybdenum of 10.2 wt. %, aluminum of 2.8 wt. %, vanadium of 1.8 wt. %, niobium of 3.7 wt. % and the balance of titanium and exhibiting pseudo-elasticity in the range of 25 and −25° C.

15. An alloy as defined in claim 1, comprising molybdenum of 11.1 wt. %, aluminum of 2.95 wt. %, vanadium of 1.9 wt. %, niobium of 4.0 wt. % and the balance of titanium and exhibiting pseudo-elasticity in the range of 50 and −25° C.

16. An alloy as defined in claim 1, which has been subjected to a heat treatment consisting of solution heating between 780 and 880 degrees C.

17. An alloy as defined in claim 1 formed into an eyeglass part.

18. A method for making a substantially nickel-free β titanium alloy, comprising the steps of alloying together:
   (a) between 10.0 and 12.0 wt. % molybdenum;
   (b) between 2.8 and 4.0 wt. % aluminum;
   (c) chromium and vanadium each between 0.0 and 2.0 wt. %; and
   (d) between 0.0 and 4.0 wt. % niobium; and
   (e) the balance titanium, there being at least one element selected from the group consisting of chromium, vanadium, and niobium.

19. A method as defined in claim 18, further comprising cold working the alloy up to 20% without significantly reducing the pseudo-elastic performance, whereby the alloy is capable of being cold formed into various shapes at ambient temperature while retaining the high spring-back characteristics of the pseudo-elastic phenomenon.

20. A method as defined in claim 18, further comprising the step of forming the alloy into an orthodontic arch wire.

21. A method as defined in claim 18, further comprising the step of forming the alloy into at least one part for eyeglasses.

22. A method as defined in claim 18, further comprising the step of forming the alloy into a medical device for use within a living body.

23. A method as defined in claim 22, wherein said medical device is chosen from the following group: (1) a stent; (2) a catheter introducer; (3) oral pins and/or plates used in maxillofacial reconstructive procedures; (4) oviduct clamp; and (5) bone staples.

24. A method as defined in claim 18 further comprising subjecting the alloy to a heat treatment consisting of solution heating between 780 and 880 degrees C.

25. A method as defined in claim 18 further comprising the step of forming the alloy into an eyeglass part.

* * * * *